United States Patent [19]

Wasserman

[11] Patent Number: 5,517,235
[45] Date of Patent: May 14, 1996

[54] METHOD AND APPARATUS FOR INSPECTING PRINTED CIRCUIT BOARDS AT DIFFERENT MAGNIFICATIONS

[75] Inventor: Harold Wasserman, Belle Mead, N.J.

[73] Assignee: Control Automation, Inc., Princeton, N.J.

[21] Appl. No.: 147,342

[22] Filed: Nov. 3, 1993

[51] Int. Cl.$^6$ .................................................. H04N 7/18
[52] U.S. Cl. ................... 348/126; 348/79; 348/87; 382/147; 382/148
[58] Field of Search .................... 348/126, 79, 87; 382/8, 147, 148; H04N 7/18

[56] References Cited

U.S. PATENT DOCUMENTS

| | | | |
|---|---|---|---|
| 4,160,263 | 7/1979 | Christy | 348/79 |
| 4,389,669 | 6/1983 | Epstein | 348/126 |
| 4,485,409 | 11/1984 | Schumacher | 348/552 |
| 4,673,988 | 6/1987 | Jansson | 348/79 |
| 4,978,220 | 12/1990 | Abramovich | 348/126 |
| 5,060,065 | 10/1991 | Wasserman | 348/126 |
| 5,245,421 | 9/1993 | Robertson | 348/126 |

Primary Examiner—Howard W. Britton
Attorney, Agent, or Firm—Weiser & Associates

[57] ABSTRACT

A printed circuit board inspection system acquires images for purposes of inspection from viewing fields defined along the surface of the printed circuit board to be inspected which can be varied in size to accommodate the density and tolerance of components associated with the printed circuit board under inspection. To this end, the cameras of the inspection head associated with the printed circuit board inspection system are provided with zoom lenses, which are capable of controlled operation responsive to the existing microprocessor systems of the printed circuit board inspection system. This allows the magnification of images acquired by the cameras to be varied, as desired, in turn varying the size of the viewing fields defined for inspection purposes. The inspection head is then operated at a rate commensurate with the size of the viewing fields which have been selected. Such operations can be varied automatically, by the printed circuit board inspection system, to effectively inspect printed circuit boards of different type and configuration. The printed circuit board inspection system can also perform successive inspections of a printed circuit board, at different magnifications.

20 Claims, 3 Drawing Sheets

METHOD AND APPARATUS FOR INSPECTING PRINTED CIRCUIT BOARDS AT DIFFERENT MAGNIFICATIONS

BACKGROUND OF THE INVENTION

This invention relates generally to systems for inspecting printed circuit boards, and more particularly, to an improved system for inspecting printed circuit boards incorporating components with close tolerances.

As is well known to persons skilled in the art, a printed circuit board is used for mounting and electrically interconnecting electrical components in a predetermined manner. To the extent possible, such printed circuit boards are constructed mechanically, using automated assembly machines which operate to reduce the often prohibitive costs of manually assembling a printed circuit board. While reducing overall costs, such automated assembly techniques have been found to give rise to a certain limited number of assembly defects such as incorrect insertions of components, and their leads or pins, as well as defects in the soldering procedures which then follow.

Originally, steps were taken to locate assembly errors of this general type through a visual inspection of each printed circuit board at a desired stage of the manufacturing process, by human operators using the naked eye, or possibly a stereo microscope or the like. However, since this procedure was found to be extremely tedious and inaccurate, as well as a relatively expensive process, steps were taken to develop automated systems for inspecting printed circuit boards, to replace such visual inspections.

Examples of devices of this general type are the Model 5511, Model 5512, Model 5515, Model 5516 and Model 5517 Printed Circuit Board Inspection Systems which are manufactured by Control Automation Incorporated of Princeton, N.J. These inspection devices generally employ a series of cameras which are mounted within a fixture (an inspection head) adapted for controlled movement relative to a printed circuit board. The inspection head is either sequentially advanced to successive viewing fields established along the surface of the printed circuit board then under inspection, or continuously advanced along the surface of the printed circuit board, to acquire images for microprocessor analysis. Any detected defects are in turn reported to the operator, for appropriate correction.

Such devices operate to enhance the accuracy of the inspection process by providing an inspection head which incorporates a series of four angled, orthogonally placed cameras, operated in conjunction with a selectively controllable light source. Through selective control of this series of cameras, and the associated light source, a variety of testing procedures are enabled including a verification of the placement of components (and their leads or pins), both before and after the soldering procedure, as well as a verification of the solder connections which are made.

Initially, such inspections were accomplished by sequentially advancing the inspection head (or the printed circuit board) through successive viewing fields, and by selectively activating the series of cameras and their associated lighting to acquire images for inspection purposes. Later, primarily in order to increase the rate at which circuit board inspections could be accomplished, such inspections were accomplished by continuously advancing the inspection head (or the printed circuit board) through its successive viewing fields, and by selectively strobing the associated lighting system to acquire images for inspection purposes. However, even this enhancement was found to have certain limitations.

Contributing to this was that concurrently with the above-described improvements to the printed circuit board inspection systems, the printed circuit boards to be inspected were themselves undergoing improvement. Techniques were developed for providing a circuit board of a given size with an increasing number of components, for performing a greater number of operations. This gave rise to closer tolerances between the respective components applied to the printed circuit board, closer tolerances between the respective features of a given component (e.g., its leads or pins), and closer tolerances between the soldered interconnections of such components, and their leads or pins, with features of the printed circuit board.

As a result, the various components associated with the printed circuit boards came to be placed closer and closer together (an increased density which is referred to in the industry as an increase in "population"), with a corresponding decrease in tolerance between the various features to be inspected. To accommodate this, it became necessary to magnify the inspections which were being performed. For example, early circuit board inspection systems typically acquired images from successive viewing fields which were on the order of one inch by one inch. Later, these viewing fields were reduced in size, to one-half inch by one-half inch. Further reduction in the size of the viewing fields would, of course, be possible to accommodate a need for higher resolution. However, reducing the size of the viewing fields to be inspected leads to corresponding disadvantages in overall operation.

Most important is that decreasing the size of the viewing fields to be inspected results in a corresponding increase in the overall amount of time which is required to inspect all of the viewing fields defined for a particular printed circuit board. However, also to be considered is that different printed circuit boards will tend to include different component "populations". This can include differences in density for different regions of a particular printed circuit board, or differences in density for different printed circuit boards which are to be inspected by a particular circuit board inspection apparatus. In many cases, this requires the definition of viewing fields of different size, for satisfactory inspections to be performed. Selecting a field of view which is too large can result in an inaccurate inspection, including the failure to identify defects as well as the false identification of defects which do not in fact exist. Selecting a field of view which is too small can unnecessarily compromise the rate at which each printed circuit board is inspected.

Consequently, the optimum field of view for a given inspection can vary widely. This has given rise to the need to change the magnification of the cameras associated with the inspection head of the printed circuit board inspection system, which has in turn limited the ability of available printed circuit board inspection systems to inspect printed circuit boards of varied configuration without requiring significant changes (in hardware and software) from job to job.

SUMMARY OF THE INVENTION

It is therefore the primary object of the present invention to provide a printed circuit board inspection system which can effectively inspect printed circuit boards bearing components of varied density and tolerance.

It is also an object of the present invention to provide a printed circuit board inspection system which can inspect printed circuit boards making use of viewing fields which can be varied in size.

It is also an object of the present invention to provide a printed circuit board inspection system having cameras which can be varied in terms of their magnification, to inspect viewing fields of different sizes.

It is also an object of the present invention to provide a printed circuit board inspection system which is sufficiently versatile to be used with various different types of printed circuit boards, bearing components of differing density and tolerance.

It is also an object of the present invention to provide a printed circuit board inspection system which is sufficiently versatile to inspect printed circuit boards of different types, at different resolutions appropriate for the density and tolerance of the components associated with the printed circuit boards to be inspected.

These and other objects which will become apparent are achieved in accordance with the present invention by providing a printed circuit board inspection system which can acquire images for purposes of inspection from viewing fields defined along the surface of the printed circuit board to be inspected which can be varied in size to accommodate the density and tolerance of components associated with the printed circuit board under inspection. To this end, the cameras of the inspection head associated with the printed circuit board inspection system are provided with zoom lenses, which are capable of controlled operation responsive to the existing microprocessor systems of the printed circuit board inspection system. This allows the magnification of images acquired by the cameras to be varied, as desired, in turn varying the size of the viewing fields defined for inspection purposes. The inspection head is then operated at a rate commensurate with the size of the viewing fields which have been selected. Such operations can be varied automatically, by the printed circuit board inspection system, to effectively inspect printed circuit boards of different type and configuration.

This also permits the printed circuit board inspection system to perform successive inspections of a printed circuit board, at different magnifications. For example, a first "rough" inspection can be performed at a relatively low magnification. Thereafter, additional "fine" inspections may be performed at higher magnifications, as desired. These additional inspections may be limited to areas of the printed circuit board which are known to include a higher density of components, or components with closer tolerances. Alternatively, these additional inspections may be limited to areas of the printed circuit board in which defects have been potentially identified, for purposes of verification. Other variations are also possible, depending upon the printed circuit board which is under inspection, and the particular inspections which are desired.

For further detail regarding a method and apparatus for implementing the printed circuit board inspection system of the present invention, reference is made to the detailed description which is provided below, taken in conjunction with the following illustrations.

DETAILED DESCRIPTION OF PREFERRED EMBODIMENTS

Figure 1:
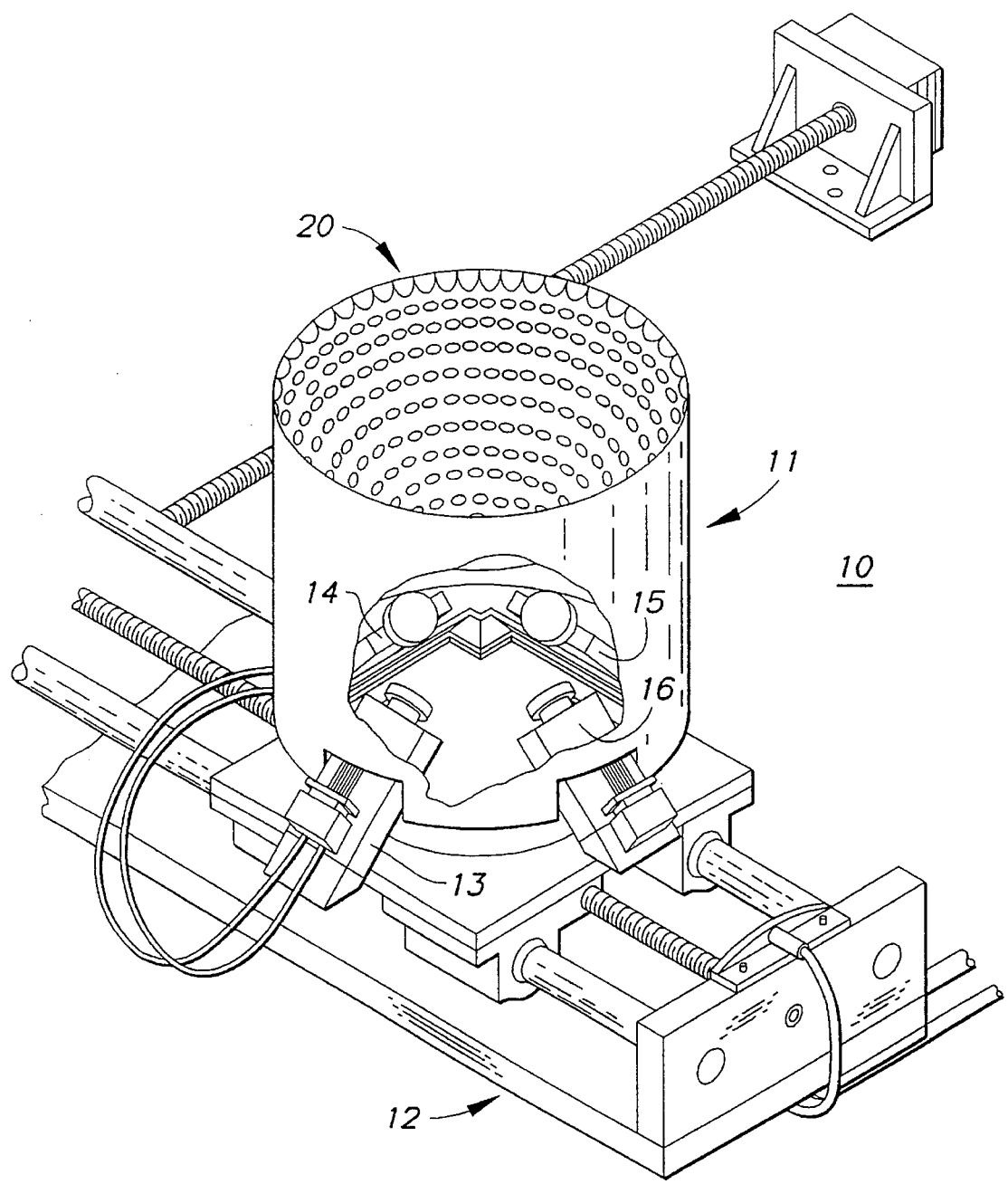
FIG. 1 is an isometric view of operative portions of a printed circuit board inspection system incorporating the improvements of the present invention.

FIG. 1 generally illustrates an apparatus 10 for inspecting printed circuit boards (not shown in FIG. 1) in accordance with the present invention. The apparatus 10 generally includes an inspection head 11 which is supported for predetermined movement in a defined plane by an X-Y table (generally designated by the reference number 12), using any of a variety of known servomotor controls. The inspection head 11 further includes a plurality of video cameras 13, 14, 15, 16 (only the video cameras 13, 16 are shown in FIG. 1), and a lighting fixture 20 for selectively illuminating regions on a printed circuit board to be inspected so that appropriate images may be acquired by the video cameras. Further detail regarding the basic construction of the apparatus 10, its various components, and its manner of operation, may be had with reference to U.S. Pat. Nos. 5,060,065 and 5,245,421.

Figure 2:
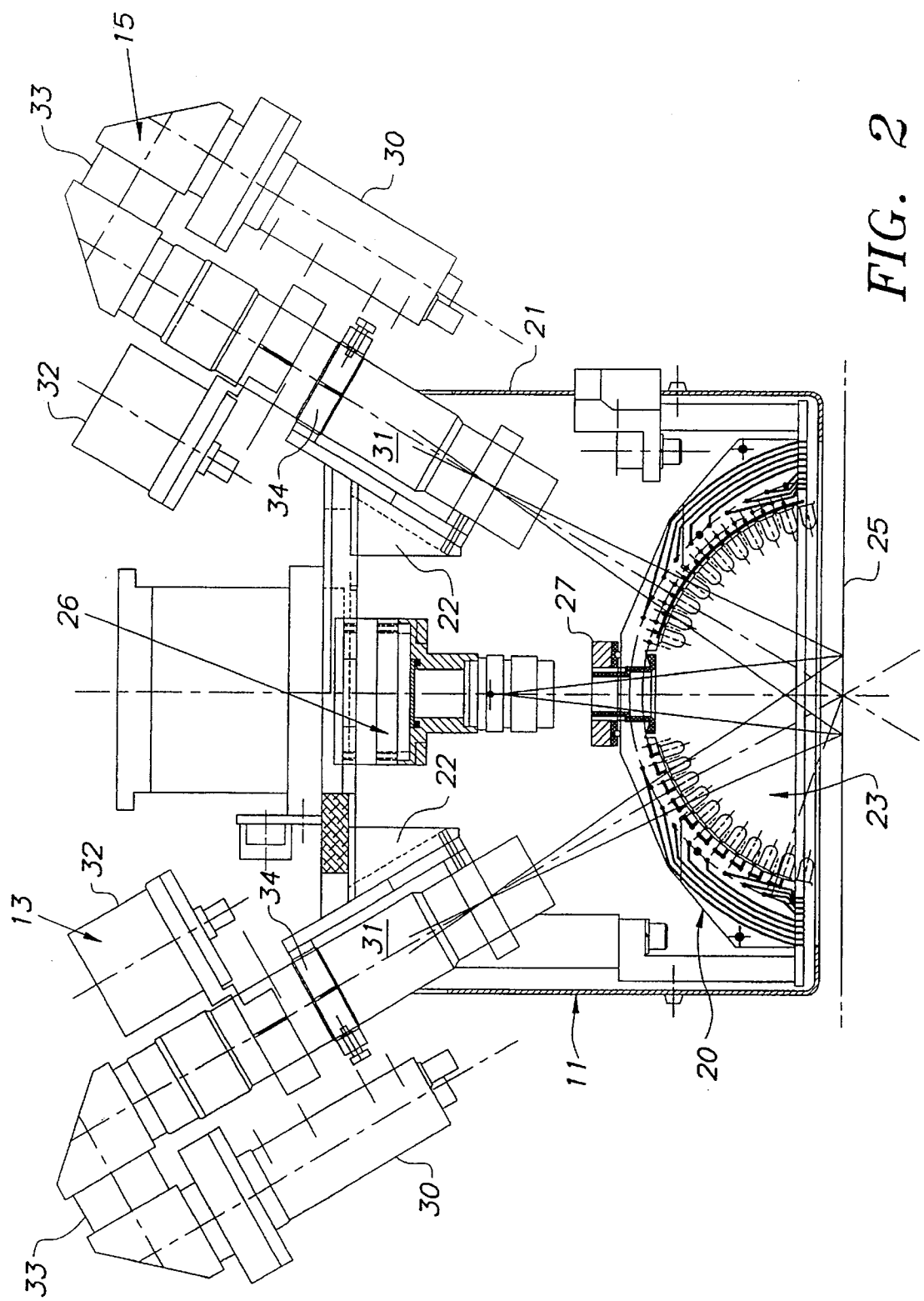
FIG. 2 is a cross-sectional view of the inspection head associated with the printed circuit board inspection system of FIG. 1.

FIG. 2 illustrates components of the inspection head 11 in greater detail. An enclosure 21 defines the inspection head 11, and receives its operative components. Two of the system's four video cameras (in this case the video cameras 13, 15) are secured to the enclosure 21 of the inspection head 11 by mountings 22 (at the angle which is desired for the inspections discussed in U.S. Pat. Nos. 5,060,065 and 5,245,421). A third video camera (the video camera 14) is located behind the structured light system which will be discussed more fully below. The fourth video camera (the video camera 16) is positioned as shown in FIG. 1. The lighting fixture 20 is mounted to the open end 23 of the enclosure 21, in registration with a printed circuit board (schematically shown at 25) to be inspected. Apertures (not shown) are provided in the lighting fixture 20 so that the video cameras 13, 14, 15, 16 can acquire images from the printed circuit board 25 using techniques which are known, for example, from U.S. Pat. Nos. 5,060,065 and 5,245,421.

The inspection head 11 additionally and preferably incorporates a projected light assembly 26, which extends through an aperture 27 formed at the base of the lighting fixture 20. The projected light assembly 26 is used to project an image onto the printed circuit board 25, which is then analyzed for purposes of compensating for deflection of the printed circuit board 25 (to account for warped printed circuit boards which may come to be inspected by the apparatus 10). For further detail regarding operation of the projected light assembly 26, and the manner in which the projected light assembly 26 is used to compensate for variations due to warped printed circuit boards, reference may be had to U.S. Pat. No. 4,978,220.

In accordance with the present invention, each of the video cameras (in the illustration of FIG. 2, the cameras 13, 15) is implemented as a CCD camera 30 which is optically coupled with a zoom lens 31. Although it is possible for the CCD camera 30 to be directly associated with the zoom lens 31, in the illustrative embodiment of FIG. 2 the CCD camera 30 and the zoom lens 31 are positioned adjacent to one another, and are optically coupled with one another at 33 (using, for example, prisms or reflecting mirrors). This arrangement is preferred to reduce the size of the overall assembly. A motor 32 (preferably a stepping motor) is coupled with the zoom lens 31, for operating the zoom lens 31 to adjust its magnification as will be discussed more fully below.

The mountings 22 are provided with appropriate clamps 34 for engaging the zoom lens 31 associated with each of the video cameras 13, 14, 15, 16, although other portions of the video cameras could be secured to the mountings 22, if desired. In any event, this serves to retain the video cameras (the zoom lenses 31) at a proper angle relative to the printed circuit board 25 to perform desired inspections in conjunction with operations of the lighting fixture 20. In the course of these operations, the CCD cameras 30 are caused to acquire images for analysis in otherwise conventional fashion. However, in accordance with the present invention, controlled operations of the motors 32 are used to vary the magnification developed by the zoom lenses 31, in turn modifying the size of the viewing fields which are defined along the surface of the printed circuit board 25. Subsequent inspections will therefore proceed with viewing fields which are defined by operations of the motors 32 (which control adjustment of the zoom lenses 31), and responsive to operations of the X-Y table 12, as follows.

Figure 3:
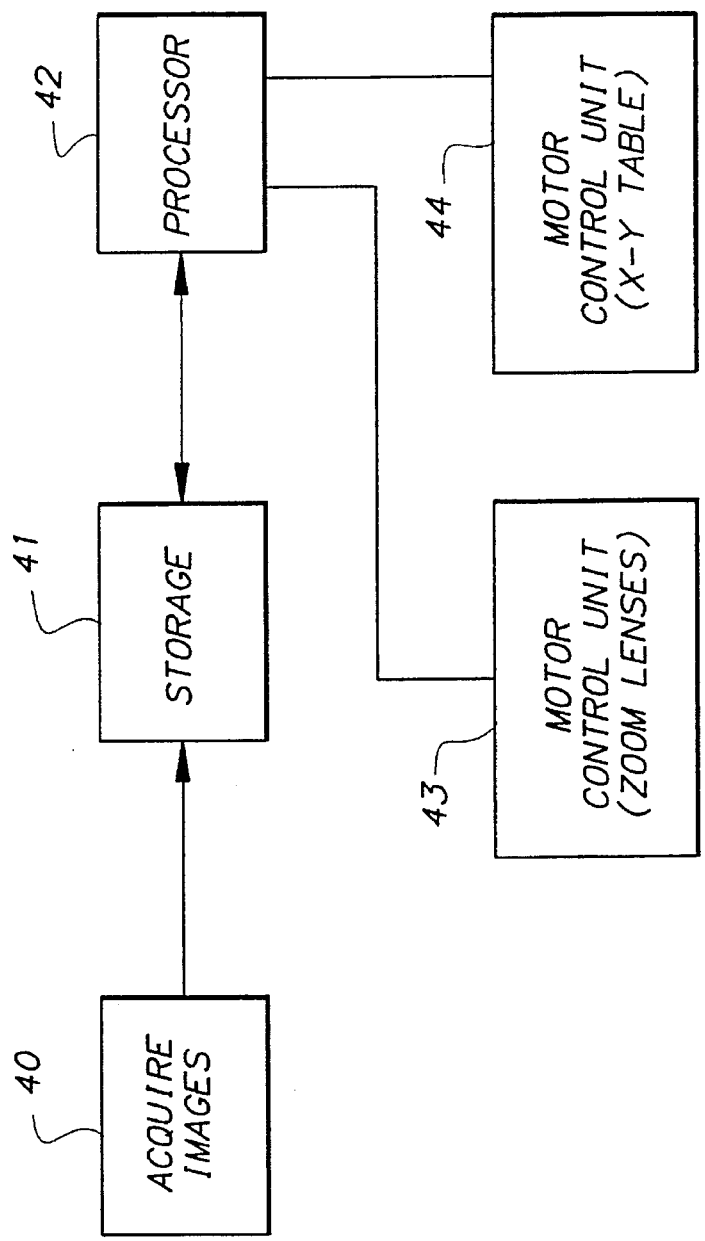
FIG. 3 is a block diagram illustrating the processing of images acquired in accordance with the present invention, making use of the inspection head of FIG. 2.

FIG. 3 is a block diagram which illustrates the manner in which images are acquired from the successive viewing fields defined along the surface of a printed circuit board under inspection, as well as the improved inspections which can be achieved in accordance with the present invention. To this end, images are appropriately acquired, at 40, from the series of video cameras 13, 14, 15, 16. Images acquired at 40 are in turn stored, at 41, for subsequent processing. Analysis of the images stored at 41 is accomplished by a processing unit 42. The processing unit 42 operates to access the acquired images stored at 41, for purposes of making the determinations necessary to inspect the field of view which is then under consideration employing techniques which are themselves known, and which otherwise correspond to inspection techniques employed by known printed circuit board inspection systems.

However, in accordance with the present invention, the viewing fields defined for the inspections which are to take place can be varied to accommodate the needs of a particular printed circuit board which is to be inspected. To this end, the processing unit 42 communicates with a motor control unit 43, which in turn communicates with the several motors 32 associated with the video cameras 13, 14, 15, 16, and a motor control unit 44, which in turn communicates with the motors (not shown) for operating the X-Y table 12. This allows the processing unit 42 to control the magnification developed by the zoom lenses 31, and to control movement of the inspection head 11 along the surface of the printed circuit board under inspection.

Since modification of the magnification developed by the zoom lenses 31 will necessarily change the size of the viewing fields under inspection, a corresponding change in the rate of movement of the inspection head 11 along the surface of the printed circuit board will also be necessary. Generally speaking, slower movements of the inspection head 11 will be required for higher magnifications, while faster movements of the inspection head 11 will be permitted for lower magnifications. In any event, the manner in which the processing unit 42 operates to accomplish inspections of a printed circuit board in accordance with the present invention is capable of variation to suit a wide variety of applications.

For example, a basic mode of operation will cause a single inspection (i.e., a single pass) of a printed circuit board under inspection by modifying the viewing fields defined for the video cameras 13, 14, 15, 16 through controlled operations of the zoom lenses 31, and by correspondingly modifying the speed at which the inspection head 11 is drawn along the surface of the printed circuit board. In such case, viewing fields of a smaller size will be defined for printed circuit boards having greater population densities and closer tolerances, while viewing fields of a larger size will be defined for printed circuit boards having lower population densities and wider tolerances. This will include corresponding decreases in the rate at which printed circuit boards of higher population density and closer tolerance are inspected, with corresponding increases in the rate at which printed circuit boards of lower population density and wider tolerance are inspected.

If desired, other more elaborate modes of operation may be accomplished in accordance with the present invention by performing the inspection of a printed circuit board in multiple passes. Such inspections are preferably accomplished by performing a first pass of the printed circuit board at a first, relatively low magnification, followed by a second pass (or even a combination of subsequent passes) of the printed circuit board at a higher magnification. Inspections during the first pass would proceed at a relatively high rate, sufficient to achieve a "course" inspection of the printed circuit board. The second pass (or subsequent passes) at the higher magnification would proceed at a lower rate, sufficient to perform a "fine", or more detailed inspection desired for a complete analysis of the printed circuit board.

Generally, the first pass will perform a complete inspection of the printed circuit board, by analyzing each of the viewing fields defined along its surface. The second pass may also perform a complete inspection of all viewing fields, at the higher level of magnification, if desired. However, it is generally preferable to employ this second pass to reinspect only those portions of the printed circuit board that require an analysis at the higher magnification level. For example, the second pass can be used to analyze only those regions of the printed circuit board bearing components of an increased population density or closer tolerance (skipping over remaining portions of the printed circuit board, which bear components of low population density and wide tolerance). Alteratively, the second pass can be used to reinspect regions of the printed circuit board where defects have been potentially identified (i.e., flagged). The second pass would then serve to confirm the presence of defects identified on the printed circuit board, or to reject incorrectly flagged defects (e.g., resulting from a first inspection at a magnification too low to adequately analyze the flagged region).

The foregoing functions are readily accomplished in software, by defining appropriate inspection routines within the processing unit 42 using techniques which are substantially identical to those presently used to accomplish inspections of printed circuit boards making use of existing equipment. Such programming would then serve to control movements of the inspection head 11, through operations of the X-Y table 12, and to control the magnification defined by the zoom lenses 31, through operations of the motors 32.

It would also be possible to perform varied inspections in accordance with the present invention, in only a single pass. In such case, movements of the inspection head 11 would be coordinated with operations of the zoom lenses 31 to perform inspections of different fields of view at different magnifications. However, such a routine is presently less preferred since the amount of time necessary to adjust the zoom lenses 31 using presently available equipment significantly exceeds the amount of time necessary to move the inspection head 11 between respective fields of view, acquire the appropriate image, and analyze the image in memory. As a result, while possible, a single inspection of this nature would proceed at a relatively slow rate, making multiple inspections (plural passes) more efficient at the present time. However, inspections in a single pass could easily be implemented in accordance with the present invention provided that faster mechanical components were made available.

It will therefore be understood that various changes in the details, materials and arrangement of parts which have been herein described and illustrated in order to explain the nature of this invention may be made by those skilled in the art within the principal and scope of the invention as expressed in the following claims. For example, while each of the four video cameras 13, 14, 15, 16 preferably includes a zoom lens 31, it is also possible for only some of the video cameras, or only one of the video cameras to be provided with a zoom lens. It is also possible to fit other types of circuit board inspection systems with zoom lenses in accordance with the present invention. For example, the single, axially disposed video camera used by other circuit board inspection systems may be fitted with such a zoom lens. Plural, vertically disposed video cameras may similarly be fitted with such zoom lenses. Such systems may be combined with angled cameras (such as the video cameras 13, 14, 15, 16), if desired. Other configurations and combinations are also clearly possible.

What is claimed is:

1. A method for automatically inspecting a printed circuit board with an apparatus including video camera means, and means for conveying the camera means across a surface of the printed circuit board, wherein the conveying means is operative to convey the camera means to and between a plurality of viewing fields defined along the surface of the printed circuit board, and wherein the method comprises the steps of:

identifying a field of view having a size appropriate for inspecting the viewing fields of the printed circuit board;

adjusting magnification of the camera means to define the field of view of appropriate size; and automatically inspecting the viewing fields defined along the surface of the printed circuit board at the adjusted magnification for the camera means, including acquiring images from the camera means which correspond to the inspected viewing fields at the adjusted magnifications, and automatically comparing the acquired images with a reference standard corresponding to a correctly assembled printed circuit board.

2. The method of claim 1 wherein a first printed circuit board having a first configuration, and a second printed circuit board having a second configuration, are to be inspected by the apparatus, and which further comprises the step of adjusting the magnification of the camera means from a first magnification for inspecting the first printed circuit board to a second magnification for inspecting the second printed circuit board.

3. The method of claim 1 wherein the surface of the printed circuit board bears components in an arrangement having a defined density and tolerance, and wherein the identifying step is performed responsive to the defined density and tolerance of the components on the printed circuit board.

4. The method of claim 3 which further includes the step of altering movement of the conveying means to a rate commensurate with the identified field of view.

5. The method of claim 1 wherein the inspecting is performed in a first pass, with a magnification adjusted to a first level and movement of the conveying means at a first rate.

6. The method of claim 4 which further includes the step of inspecting the printed circuit board in a second pass, with a magnification adjusted to a second level different from the first level and movement of the conveying means at a second rate different from the first rate.

7. The method of claim 6 wherein the second magnification is greater than the first magnification.

8. The method of claim 7 wherein the second rate is less than the first rate.

9. The method of claim 6 wherein only selected portions of the printed circuit board are inspected in the second pass.

10. The method of claim 9 wherein the surface of the printed circuit board bears components in an arrangement having a defined density and tolerance, and wherein the selected portions are portions of the printed circuit board having a density and tolerance above a selected threshold.

11. The method of claim 9 wherein the surface of the printed circuit board bears components in an arrangement having a defined density and tolerance, and wherein the selected portions are portions of the printed circuit board having a defect identified during the inspecting in the first pass.

12. In an apparatus for automatically inspecting a printed circuit board, including video camera means, and means for conveying the camera means across a surface of the printed circuit board, wherein the conveying means is operative to convey the camera means to and between a plurality of viewing fields defined along the surface of the printed circuit board, the improvement which comprises:

processor means for identifying a field of view having a size appropriate for inspecting the viewing fields of the printed circuit board;

means for adjusting magnification of the camera means to define the field of view of appropriate size; and means associated with the processor means, for automatically inspecting the viewing fields defined along the surface of the printed circuit board at the adjusted magnification for the camera means, including means for acquiring images from the camera means which correspond to the inspected viewing fields at the adjusted magnifications, and means for automatically comparing the acquired images with a reference standard corresponding to a correctly assembled printed circuit board.

13. The apparatus of claim 12 wherein a first printed circuit board having a first configuration, and a second printed circuit board having a second configuration, are to be inspected by the apparatus, and which further comprises means for adjusting the magnification of the camera means from a first magnification for inspecting the first printed circuit board to a second magnification for inspecting the second printed circuit board.

14. The apparatus of claim 12 wherein the surface of the printed circuit board bears components in an arrangement having a defined density and tolerance, and wherein the processor means operates responsive to the defined density and tolerance of the components on the printed circuit board.

15. The apparatus of claim 14 which further includes means for conveying the camera means at a rate commensurate with the identified field of view.

16. The apparatus of claim 12 wherein the magnification adjusting means is a zoom lens associated with the camera means.

17. The apparatus of claim 16 which further includes motor operated means for operating the zoom lens to adjust the magnification of the zoom lens.

18. The apparatus of claim 17 wherein the motor operated means is coupled with the inspecting means, for control of the motor operated means responsive to operations of the inspecting means.

19. An apparatus for automatically inspecting a printed circuit board, including video camera means, and means for conveying the camera means across a surface of the printed circuit board, wherein the camera means is coupled with a zoom lens for adjusting magnification of the camera means to define a field of view appropriate for inspecting the viewing fields of the printed circuit board, wherein the conveying means is operative to convey the camera means to and between the plurality of viewing fields defined along the surface of the printed circuit board, and wherein the apparatus further includes processor means for automatically inspecting the viewing fields at the adjusted magnification, including means for acquiring images from the camera means which correspond to the inspected viewing fields at the adjusted magnification, and means for automatically comparing the acquired images with a reference standard corresponding to a correctly assembled printed circuit board.

20. The apparatus of claim 19 which further comprises motor operated means coupled with the zoom lens, for operating the zoom lens to adjust the magnification of the zoom lens.

* * * * *